United States Patent [19]

Merkatoris et al.

[11] Patent Number: 5,389,173
[45] Date of Patent: Feb. 14, 1995

[54] APPARATUS AND PROCESS FOR MAKING DISPOSABLE DIAPER TYPE PRODUCTS

[75] Inventors: John R. Merkatoris; Gary E. Johnson, both of Green Bay, Wis.

[73] Assignee: Paper Converting Machine Company, Green Bay, Wis.

[21] Appl. No.: 131,285

[22] Filed: Oct. 4, 1993

Related U.S. Application Data

[63] Continuation-in-part of Ser. No. 984,468, Dec. 2, 1992, abandoned.

[51] Int. Cl.⁶ .................. A41B 13/00; A61F 13/15
[52] U.S. Cl. .................. 156/164; 156/161; 156/229; 156/494; 156/495; 604/385.2
[58] Field of Search ............. 156/160, 161, 163, 164, 156/229, 494, 554, 555, 495; 2/400; 604/385.2

[56] References Cited

U.S. PATENT DOCUMENTS

| | | |
|---|---|---|
| 4,081,301 | 3/1978 | Buell . |
| 4,293,367 | 10/1981 | Klasek et al. . |
| 4,464,217 | 8/1984 | Dickover et al. . |
| 4,507,163 | 3/1985 | Menard . |
| 4,642,109 | 2/1987 | Bradley et al. . |
| 4,675,068 | 6/1987 | Lundmark . |
| 4,764,234 | 8/1988 | Smits et al. . |
| 4,786,345 | 11/1988 | Ales et al. . |
| 4,801,245 | 1/1989 | Dussaud et al. . |
| 4,915,767 | 4/1990 | Rajala et al. . |
| 4,917,695 | 4/1990 | Villez . |
| 4,917,746 | 4/1990 | Kons et al. . |
| 5,147,489 | 9/1992 | Nomura et al. . |
| 5,236,539 | 8/1993 | Rogberg et al. .......... 156/495 |
| 5,275,676 | 1/1994 | Rooyakkers et al. ........ 156/495 |

FOREIGN PATENT DOCUMENTS

| | | |
|---|---|---|
| 0475419 | 3/1992 | European Pat. Off. . |
| 428363 | 1/1992 | Japan . |
| 428364 | 1/1992 | Japan . |
| 2234157 | 1/1991 | United Kingdom . |
| 2248380 | 4/1992 | United Kingdom . |
| 89/00189 | 10/1989 | WIPO . |
| WO92/07531 | 5/1992 | WIPO . |

*Primary Examiner*—Jeff H. Aftergut
*Attorney, Agent, or Firm*—Tilton, Fallon, Lungmus & Chestnut

[57] ABSTRACT

Apparatus for producing disposable diaper type products such as diapers per se and training pants in which leg elastic strands are captured between a pair of webs which are thereafter united with a fluff pad-equipped web and wherein guide members are employed for traversing the elastic strands to abut leg openings in the diaper type product.

11 Claims, 5 Drawing Sheets

APPARATUS AND PROCESS FOR MAKING DISPOSABLE DIAPER TYPE PRODUCTS

This application is a continuation-in-part of application Ser. No. 984,468, filed Dec. 2, 1992, now abandoned.

BACKGROUND AND SUMMARY OF INVENTION

This invention relates to apparatus for making disposable type diaper products and, more particularly, diaper products (such as diapers per se and training pants) wherein there is a contoured leg elastic. A representative prior art patent is U.S. Pat. No. 4,801,345.

The principal object of this invention is to create elastic gathers around the leg openings in disposable products such as the above-mentioned infant diapers and training pants Two problems are involved which the invention has solved.

A first problem lies in the inability to hold the elastic in the desired contour. Once the elastic strand or strands are laid down onto the adhesive-equipped web, the cross machine forces tend to roll or slide the elastic, reducing the amplitude of the profile. The amount of change is a function of adhesive "green tack", line speed and pressing means.

A second problem lies in the fact that elastic profiles may differ significantly from the profile program for the guide means for the elastic. This is due to the length of elastic between the guide means and the adhesive-equipped web. Typically one to two inches of free elastic are involved. The guide would then need to travel the distance greater than the desired profile to account for the transverse distance lost in the free span of the elastic.

The first listed problem has been efficiently solved through the provision special guide means in combination with a pair of nip rolls and the second problem relating to maintaining the desired profile has been solved by trapping the elastic strands between two webs, typically one of nonwoven and one of polyethylene.

Japanese Applications 4028-363-A and 4028-364-A show introducing contoured leg elastic strands between two plies of the diaper, U.S. Pat. No. 5,147,487 which show a single web plus contoured elastic strands passing between a pair of rollers and PCT WO 89/09550 which shows contoured strands applied to a web.

According to the instant invention, the two webs, at least one of which has adhesive, are passed along with the elastic strands into a two-roll nip and subsequently travel in partial wrapping engagement with one of the rolls. Thus, the outer web tension is converted to pressure so that the strand profile is preserved by giving the glue time to set so as to maintain the width of the webs.

BRIEF DESCRIPTION OF DRAWING

The invention is described in conjunction with the accompanying drawing in which.

DETAILED DESCRIPTION

Figure 1:
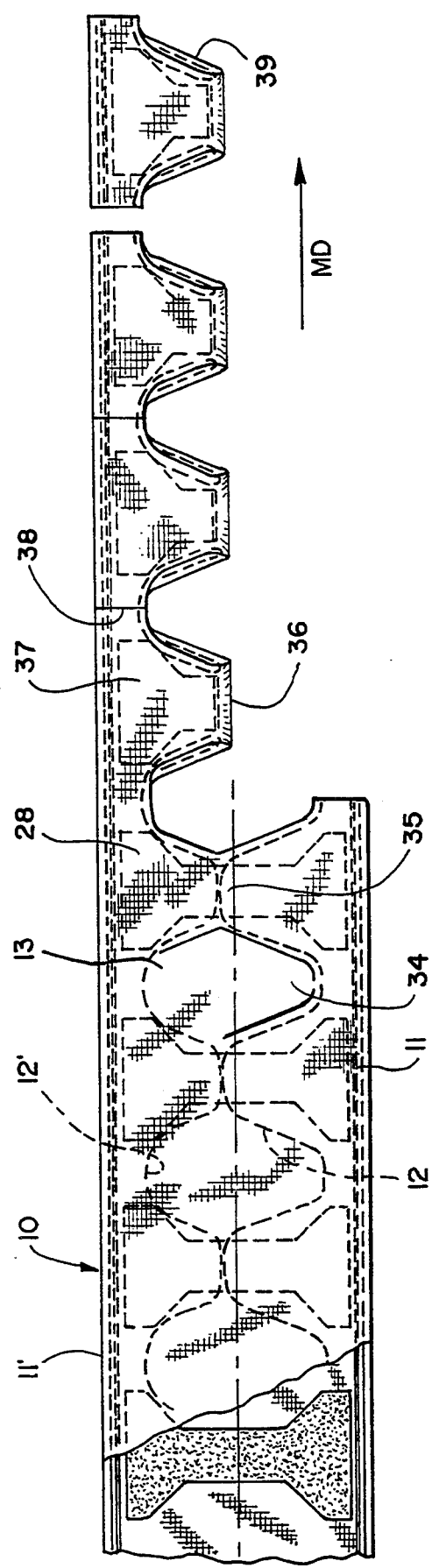
FIG. 1 is a top plan view, somewhat schematic, of a construction of disposable training pants.

In the illustration given and with particular reference to FIG. 1, the numeral 10 designates generally a diaper type construction which advantageously can be used for training pants. It is made with the waist elastic 11 extending in the machine direction MD and the leg elastics 12, 12' are displaced in the cross machine direction to circumscribe the areas 13 which define leg openings. It is also within the purview of the invention to do a similar profile for products made in the other direction, i.e., with waist elastics in the cross machine direction. Still further, each of the leg elastics 12, 12' can be single strand (one per side of the opening 13) or preferably multiple strand. Further reference will be made to FIG. 1 after describing the apparatus and method for installing the elastic strands.

Figure 2:
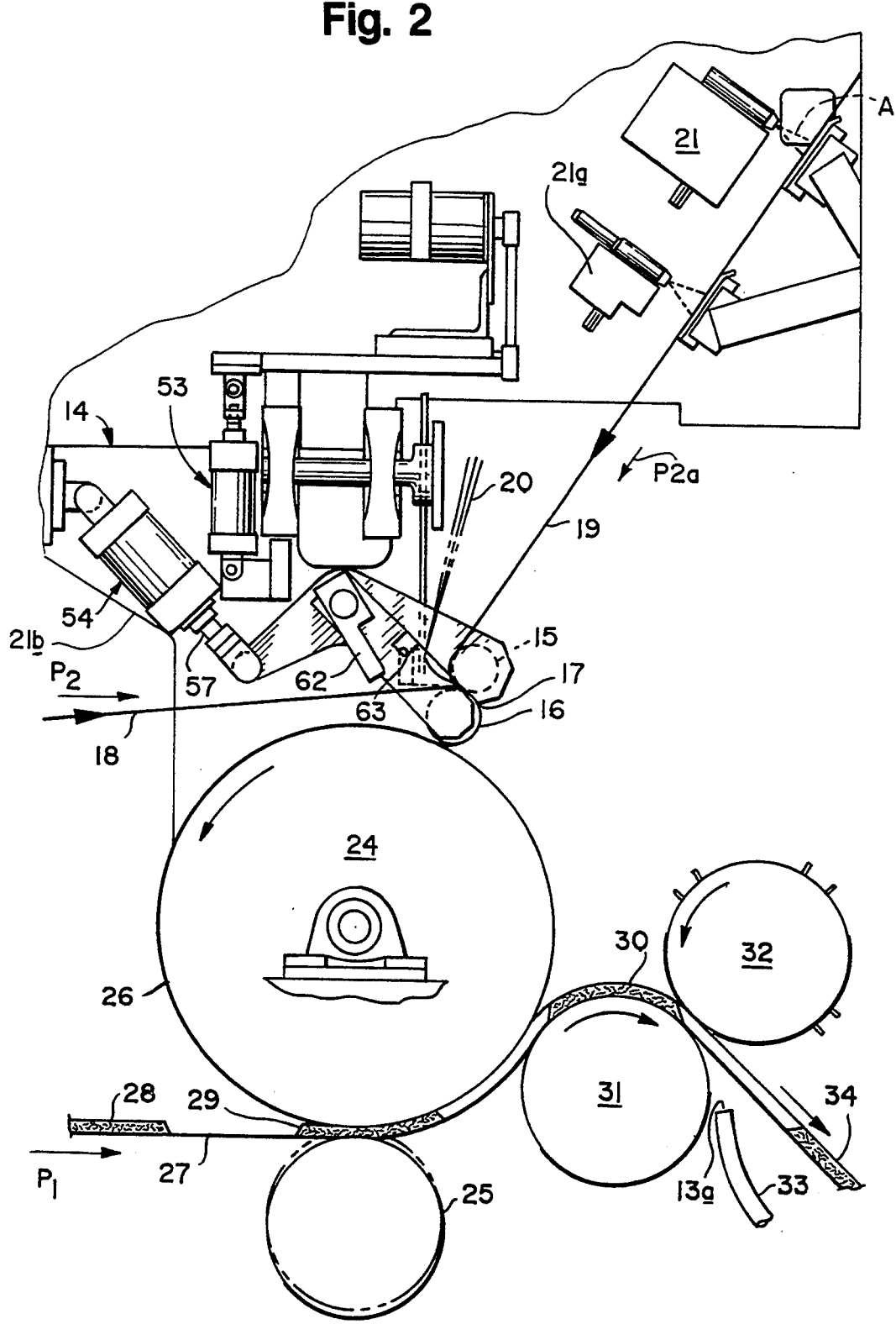
FIG. 2 is a side elevational view of apparatus employed in the production of the diaper type training pants illustrated in FIG. 1.
Figure 6:
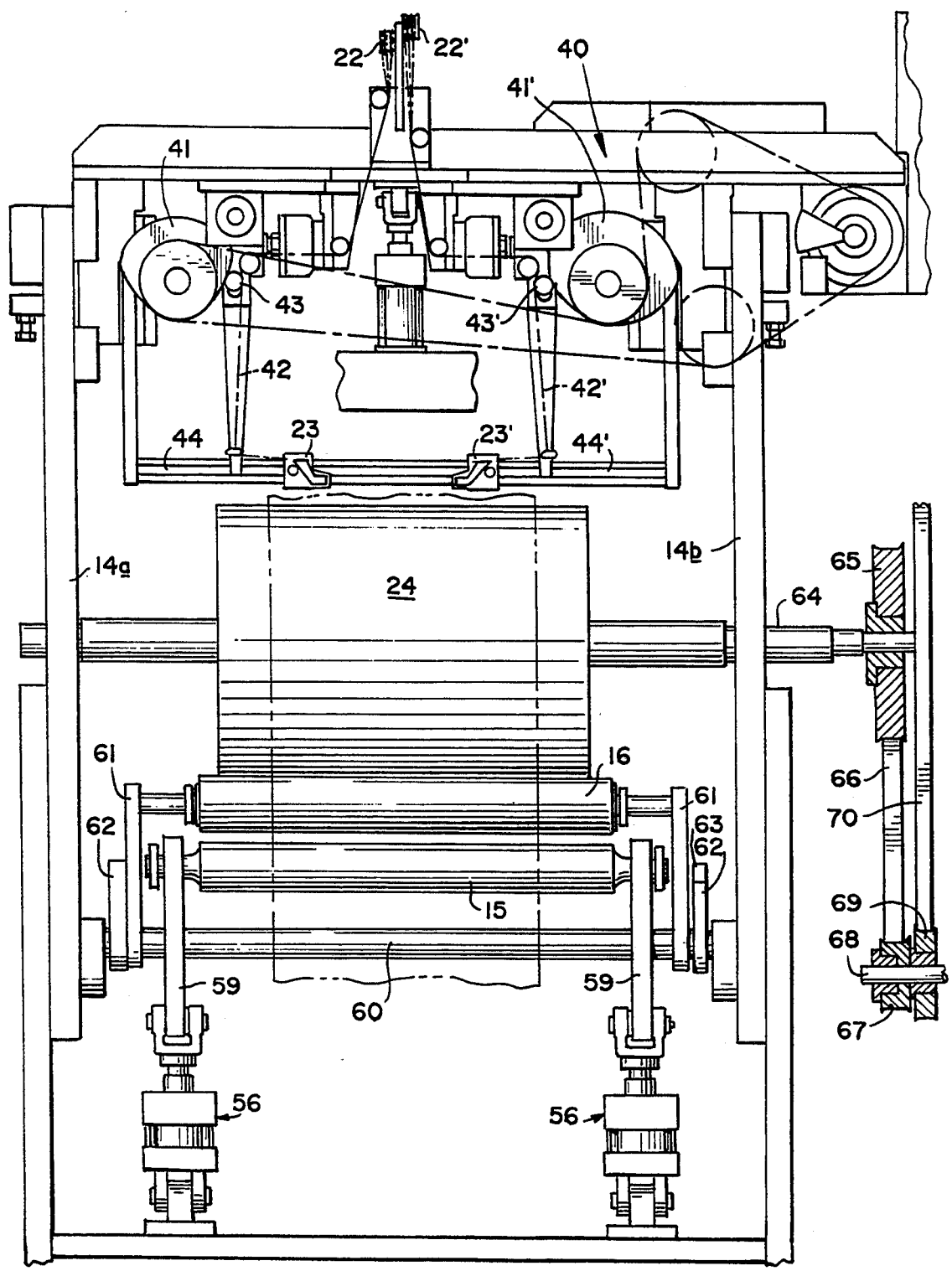
FIG. 6 is a developed end elevational view of the apparatus of FIG. 2.

Now referring to FIG. 2, the numeral 14 designates generally the frame of the machine which conventionally has a pair of side frames as at 14a, and 14b (see FIG. 6). FIG. 6 is a projected version, illustrating the various parts in spaced relation so as to better appreciate their relationship. The actual relationship of the various rolls, for example, is featured in FIG. 2.

As seen in the central part of FIG. 2, the frame 14 rotatably supports a pair of nip-forming rolls 15 and 16 which develop a nip 17. This nip receives, for example, a polyethylene web 18 (center left) and a nonwoven web 19 (upper right). Sandwiched between the webs 18, 19 are one or more individual elastic strands 20—three being shown in the upper center of FIG. 2.

Figure 3:
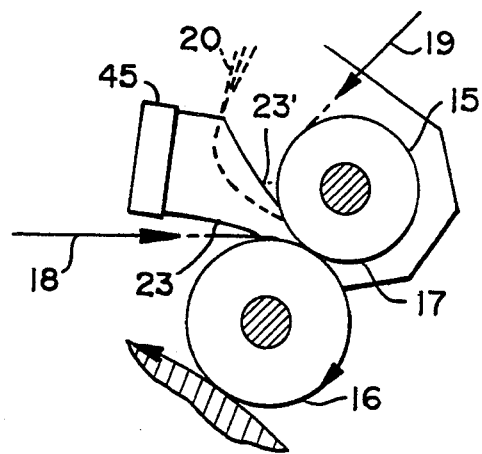
FIG. 3 is an enlarged side elevational view partly in section of the elements located centrally of the machine in FIG. 2.

Now referring to FIG. 3, the nip rolls 15 and 16 just referred to are shown in larger scale and also seen are the webs 18 and 19. Each of webs 18, 19 may be advantageously equipped with adhesive such as would be applied, for example, to the web 19 by the nozzles 21, 21a—see the upper right portion of FIG. 2. Adhesive (A) provided by a transverse line of nozzles 21 is employed to unite the strand or strands 20 to the web or webs and also unite the webs 18, 19 together. Two laterally spaced nozzles 21a are employed for the securing waistband elastic (not shown) longitudinally of the web.

Operation Generally

Figure 4:
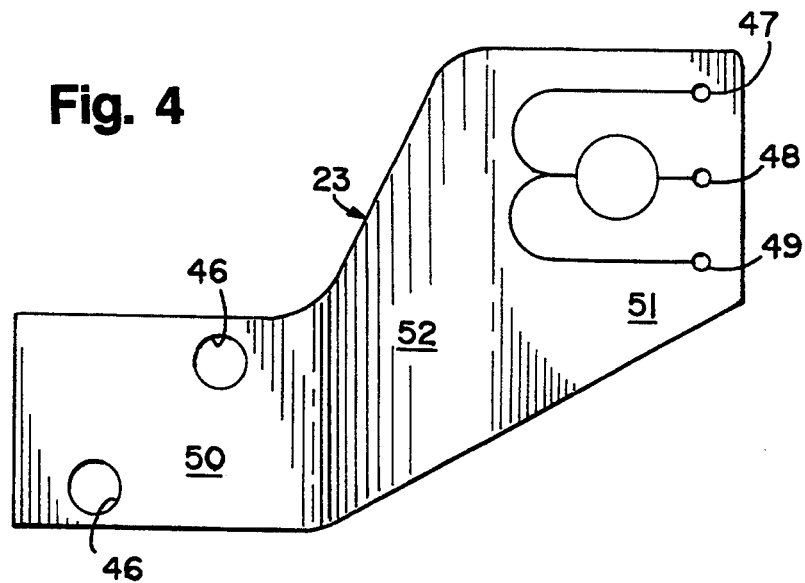
FIG. 4 is a top plan view of a guide element for transversely shifting the elastic strands.
Figure 5:
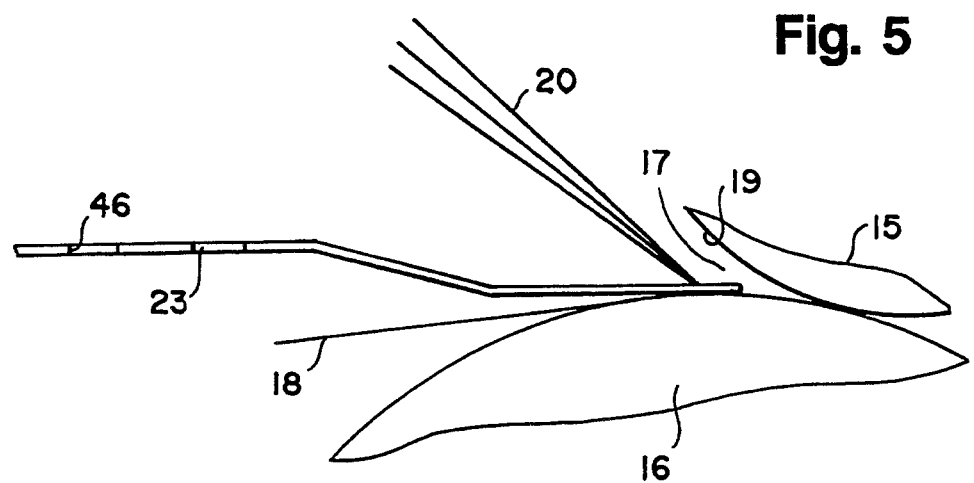
FIG. 5 is a fragmentary side elevational view of the guide element of FIG. 4 in the process of guiding elastic strands onto one of the nip rollers.

Two pluralities (12, 12'—see FIG. 1) of strands 20 are provided from spools 22, 22' mounted on frame 14—see the upper central portions of FIGS. 2 and 6. These are directed into a pair of guide means 23, 23'—see FIG. 3. The details of the guide member 23 for directing three strands 20 into the nip 17 are seen in FIGS. 4 and 5. In FIG. 5, only the lower guide member 23 is seen projecting into the nip 17 and pressing against the web 18.

As indicated above, trapping of the elastics overcomes the first problem discussed above, the normal inability of diaper/training pant machines to hold the elastic strands in the desired contour. The trapping of the elastic provided by the invention results in pressing and holding the elastic without contaminating the rolls in the machine.

Referring to FIG. 3 (which is an enlarged view of the guide members 23, 23' and the nip-forming rolls 15, 16), the guide member 23', for example, rides on the adhesive-equipped web 19 while the guide means 23 rides on the web 18. Each web may have an adhesive pattern or profile laid on in the same fashion as the nozzle 21' lays down the pattern on web 19. Nozzles like those at 21, 21' can be employed relative to the web 18.

The guide members 23, 23' press the elastic strands 20 directly onto the web. Since the guide members (see FIG. 5) extend into the nip—virtually to the point of tangency of the rolls 15, 16—the adhesive quickly grips the strands 20. In this fashion, the profile of the strands follows the profile developed by travel of the guide members very closely. This overcomes the second mentioned problem where the elastic profiles could differ significantly from the profile described or followed the elastic guide means.

Referring to FIG. 2, the strands 20 now captured between webs 18, 19 proceed around a drum 24 which operates in conjunction with a bump roll 25 to apply the composite laminated web 26 to a basic nonwoven web 27.

The bump roll 25 is conventional in the art and is reciprocably urged against the drum 24 to move between the solid line position illustrated wherein the roll bears against the pad 28 and the dashed line position 25' where it bears against the three web laminate consisting of the united webs 26 and the web 27 between pads.

The nonwoven web 27 constitutes the inner web of the ultimate training pants or diaper and supports thereon fluff pads as at 28. As the web 27 equipped with pads 28 passes through the nip 29 between the drum 24 (which may have a vacuum assist) and roll 25, the two web-composite or laminate 26 is adhered to the basic or inner nonwoven web 27 to provide a diaper product having the following in proceeding from the interior: a nonwoven web 27, pad 28, non-woven web 19, elastic strands 20 and polyethylene web 18.

The non-woven web 27 is equipped with adhesive to integrate the fluff pads 28 and the laminate 26 thereto to provide the multilayer product 30. As seen in FIG. 2, this multi-layer product web passes around anvil roll 31 which, with its cooperating die knife roll 32, is rotatably mounted on the frame 14. The rolls 31, 32 operate to cut out chips 13a which result in the leg openings 13—see FIG. 1. The cutouts or chips 13a are advantageously removed by a vacuum waste tube 33—see FIG. 2 at the lower right. This results in the construction 34 which is also seen at the left in FIG. 1.

Now referring to FIG. 1, the leg elastics 12, 12' are seen to cross over the fluff pads 28 at 35 and follow the contour of the leg openings 13. After the diaper construction 10 has been achieved, the construction can be folded over as at 36 to provide the configuration designated 37, the sides are superposed as at 38. Thereafter the individual units can be severed from the continuous stream to provide the final diaper or pant 39.

Apparatus Summary

Summarizing, there is a frame 14 which defines a generally horizontally extending first path $P_1$ (FIG. 2) between side frames 14a and 14b (FIG. 6). There are means on the frame including drum 24 and roll 25 for advancing a first web 27 equipped with fluff pads 28. There are a pair of rolls 15, 16 mounted on the frame 14 and providing a nip 17—these rolls 15, 16 being aligned with the first path $P_1$ and vertically spaced therefrom.

The frame 14 also defines a second path including parts $P_2$, $P_{2a}$ along which are respectively advanced second and third webs 18, 19 toward and into the nip 17 between rolls 15, 16. The rolls 15, 16 serve to advance the webs 18, 19. The part $P_{2a}$ of the second path has means in the form of nozzles 21, 21a for equipping one of the webs 19 with adhesive (A). In some instances it may be advantageous to apply adhesive to both webs or just to the web 18 alone. If so, an adhesive nozzle means can be mounted on the frame 14 adjacent the position 21b.

There is also provided a means including spools 22, 22' and guide means 23, 23' for feeding a continuous elastic strand 20 the nip 17 between the second and third webs 18, 19 and into contact with the adhesive laid down by nozzles 21, 21'. This results in uniting the second and third webs with the strand or strands being united to the second and third webs. The guide means 23, 23' are mounted on the frame closely adjacent to the nip 17 and serve to shift the strand laterally.

The drum 24 and bump roll 25 constitutes means for uniting the first web 27 with the already united second and third webs 18, 19.

The pair of rolls 15, 16 are positioned relative to the first path P, so as to have the united second and third webs 18, 19 travel in partial wrapping engagement with the roll 16 as shown in FIG. 2. More particularly the rolls 15, 16 are positioned closely adjacent the drum 24 and the webs 18, 19 are maintained under tension until they engage the first web 27.

Shifting Features

Reference is now made to FIG. 6 where the numeral 40 designates generally the means for traversing the guide means 23, 23'. These advantageously can take the form of cams 41 and 41' which are contoured to develop the desired profile. Pivotally mounted on a part of the frame are rods 42 and 42' which are equipped with cam followers at 43 and 43' so as to develop a traversing motion based upon the cam profile. At their lower ends (as shown), the rods 42, 42' carry the elastic guide members 23, 23' which are mounted for transverse sliding motion on rods 44 and 44'. As seen in FIG. 2, these guide members lead the various elastic strands 20 into the nip 17 between the rolls 15, 16.

A variety of means may be employed for achieving the transverse movement of shifting of the guide means 23, 23'. As shown, cams develop a mechanical linkage for this purpose. Alternatively, translating screws or crank arms can also be applied for mechanical shifting and electricity may be employed through motor operated belts. Still further, the elastic feed means can be achieved through servo motors which drive feed rollers on a side shifting carriage.

Reference is now made to FIG. 4 which features the guide means such as would be seen at 23 and which is adapted to apply the elastic strands. The same construction can be employed to apply 1, 2, 3, etc. elastic strands. The device 23 of FIGS. 4 and 5 includes a flat spring steel member which can be suitably mounted on the machine frame via a bracket 45—see FIG. 3. Suitable bolt openings as at 46 are provided in the supported end of each resilient guide means 23, 23'.

Each of the members 23, 23' at free or cantilevered end is equipped with eyelets 47-49 respectively—through which the strands are threaded. The members 23 have a mounting end 50 and eyelet end 51 and a transition portion 52 in between. This portion 41 disposes the ends 50, 51 in different parallel planes and provides advantageous arm flexing means.

As can be appreciated from a consideration of FIGS. 4 and 5, the eyelets 47-49 have the strands extending therethrough so that the eyelets do not bear directly against the adhesive-equipped web 18 but instead bear against the strand or strands 20. These strands typically have a discrete thickness of the order of about 0.020" and a width of 0.060" so that there is relatively little pick-up of adhesive from the adhesive-equipped web 18 onto the guide. However, should some adhesive be picked up by the eyelets, this is advantageously wiped off by virtue of the shifting of the guide means incident to developing the desired profile for the elastic strands. In other words, the strands move back and forth in the eyelets as the guide means moves transversely to develop the desired profile. This develops an advantageous wiping engagement of the strands with the guide means to remove any adhesive picked up thereby. This could result from the mounting of the guide means 23, 23' to press the strands against an adhesive-equipped web.

Further, with the arrangement of structural features, it is easy to provide for pivoting of the guide means 23, 23' and connected elements to facilitate thread-up.

Pivot Features

Figure 7:
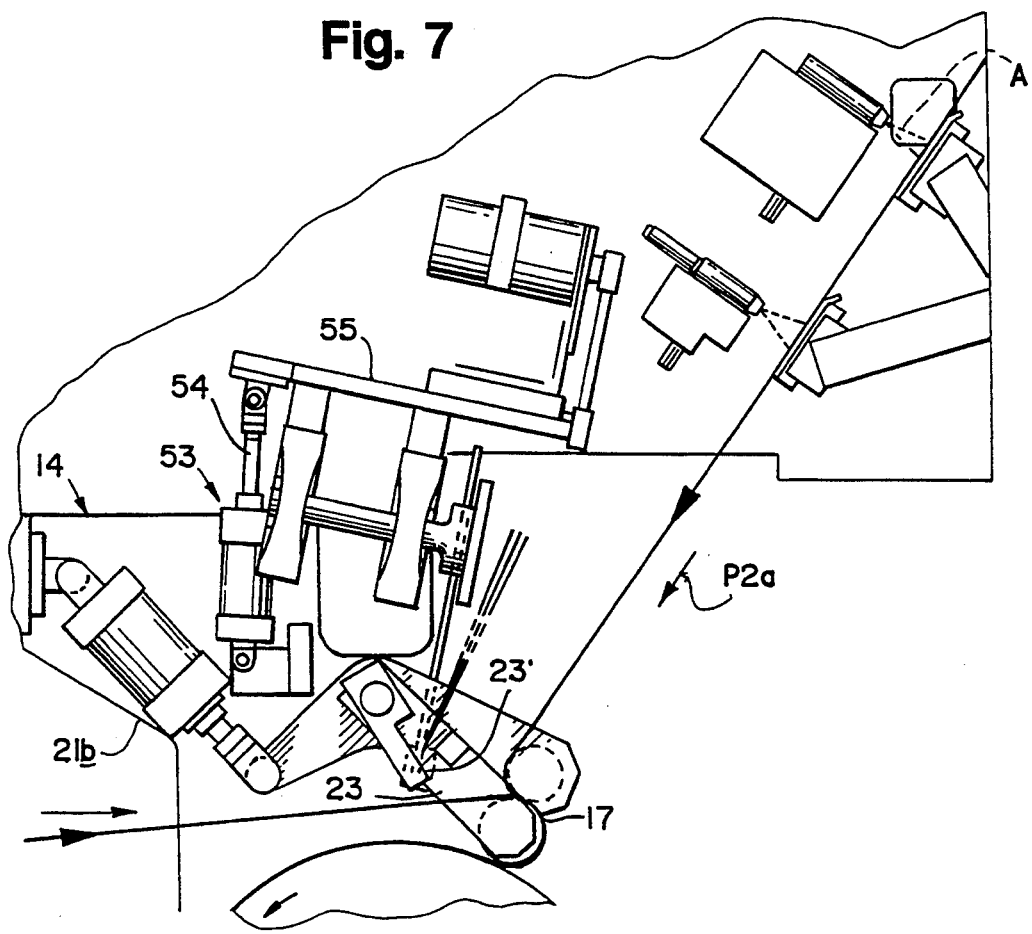
FIG. 7 is a fragmentary side elevational view similar to FIG. 2 but showing the parts in a different condition, i.e., where the guide elements are pivoted away from their positions in FIG. 2.
Figure 8:
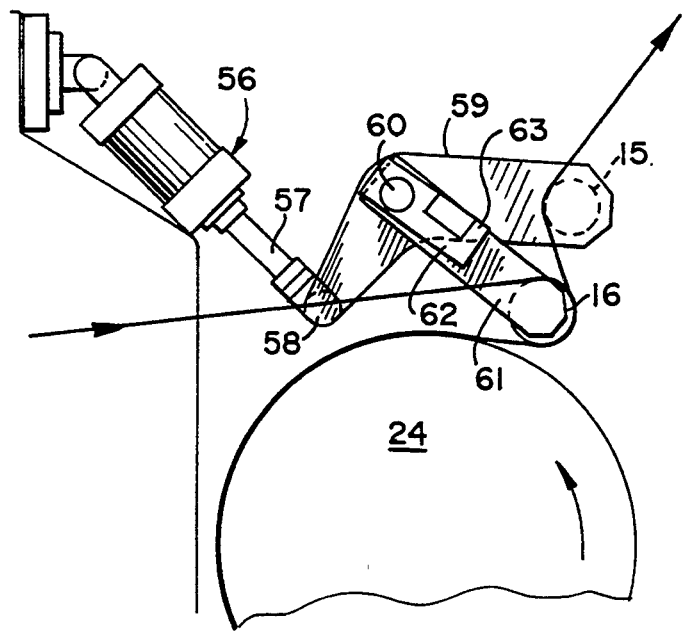
FIG. 8 is another fragmentary side elevational view of the apparatus seen in FIG. 2 but showing the nip rolls in a different condition, i.e., pivoted away from each other and from the larger advancing drum.

Reference is now made to FIGS. 7 and 8. In FIG. 7 the guide means 23, 23' have been pivoted clockwise from the showing in FIG. 2 and out of the nip 17. This is achieved through a cylinder and piston rod unit generally designated 53 (see the upper left hand portion of FIG. 7) which has its rod 54 extended—as compared with the showing in FIG. 2. This pivots a subframe 55 which carries the translating means and the various intermediate members terminating in the guide means 23, 23'. The subframe 55 is pivotally mounted on the frame 14 and the pivoting of the subframe 55 to the position of FIG. 7 exposes the guide means 23, 23' for thread-up, size change, etc.

Thereafter, a second pivoting action is performed. This employs the cylinder and piston rod unit generally designated 56 (see the upper left hand portion of FIG. 8). The cylinder and piston rod unit 56 is also seen in FIG. 2 where the rod 57 is retracted compared to the showing in FIG. 8. The work end of the rod 57 is pivotally connected as at 58 to a generally L-shaped arm 59. Intermediate its ends, the arm 59 is affixed to a cross-shaft 60 which is rotatably mounted in the side frames 14a, 14b. More particularly, a pair of L-shaped arms 59 are provided (to support both ends of the roll 15) as can be appreciated from the lower portion of FIG. 6.) So also are provided a pair of cylinder and piston rod units 56. Thus, as the piston rod 57 is extended, the L-shaped arm 59 is pivoted counterclockwise to raise the roll 15 away from the roll 16 which is in contact with the drum 24.

This same counterclockwise movement also moves the roll 16 away from the surface of the drum 24. For that purpose, the roll 16 is carried by arms 61 which are rotatably mounted on the shaft 60. Fixed to the shaft 60 is a lever arm 62 which moves from its FIG. 2 position into engagement with a block 63 on each arm 61. As the L-shaped arm 59 continues to pivot, it causes the lever arm 62 to bear against the block 63 and thus move the arms 61 counterclockwise—to position the roll 16 away from the surface of the drum 24.

Inventive Method

In the practice of the inventive method, the following steps are performed in making disposable diapers having leg opening areas:

1. Advancing a fluff pad-equipped first web (27) along a generally horizontal first path $P_1$,
2. advancing second and third webs (18, 19) along a path ($P_2$, $P_{2a}$) generally parallel to the first path and into a nip (17) provided by a pair of rolls (15, 16),
3. applying adhesive (A) to at least one of the second and third webs (18, 19) prior to the entry thereof into the nip,
4. feeding a continuous elastic strand 20 into the nip and between the second and third webs and into contact with the adhesive while controlling the position of the strand at a point closely adjacent the nip through eyelets (47-49) in guide means (23) and while the strand is resiliently pressed against the adhesive-equipped web just prior to entering the nip,
5. shifting the strand laterally about leg opening areas (13) in the second and third webs by oscillating or travering means (40),
6. uniting the second and third webs with the strand therebetween by passing all three through the nip 17, and
7. uniting the now-united second and third webs (26) with the first web (27) while maintaining the united second and third webs under tension until engagement with the first web—this tension being particularly effective when the second and third webs travel in partial wrapping engagement with the nip forming roll 16 adjacent the drum 24.

As pointed out above, there is an advantageous conversion of the tension in the outer web (19 in the illustration given) to pressure so as to effectively clamp the strand, i.e., maintain the desired profile. This clamping action results in substantially immobilizing the strand in the desired position, i.e., predetermined profile—see FIG. 1.

Although tensioned webs are conventional in the converting art, particularly relating to disposable diapers and the like, there is here a novel usage of the tension to immobilize the strand or strands. Because the outer web 19 in the illustration given has to travel along a larger radius than the inner web 18—as they both travel around a part of the periphery of the roll 16—there is a novel use of the tension as the webs 18, 19 approach the drum 24.

In the illustration given, the drum 24 is equipped with an axially extending shaft 64 on which is mounted a pulley 65 (see the lower right hand portion of FIG. 6). When the rolls 15, 16 are pivoted into operable position as seen in FIG. 2, the rolls 15 and 16 are effectively driven by the drum 24. Thus, whatever tension is provided in the webs 18, 19 it is also maintained throughout the travel of these webs into the nip 17, with the surface of roll 16 and with the surface of the roll 24. Normally, tension is provided on the webs 18, 19 upstream of the nip 17 by virtue of draw rolls (not shown) provided in connection with the unwinds for the various webs 18, 19 and 27. A slight tension—of the order of one pound per transverse lineal inch is maintained in the webs 18, 19 and 27 by virtue of the conventional unwinds in combination with the powered drum 24 and its driven idler rolls 15, 16.

Completing the drive in FIG. 6, we provide a belt 66 entrained on the pulley 65 and further entrained on a pulley 67 mounted on a drive shaft 68. This receives rotational power from a motor (not shown). Also mounted on the drive shaft 68 is a second pulley 69 over which is entrained a belt 70 and which is connected to the elements at the upper part of FIG. 6 for providing traverse motion of the guide means 23, 23'.

While in the foregoing specification a detailed description of an embodiment of the invention has been set down for the purpose of explanation, many variations in the details hereingiven may be made by those skilled in the art without departing from the spirit and scope of the invention.

We claim:

1. A method for making disposable diapers having leg opening areas comprising the steps of: advancing a fluff pad-equipped first web along a generally horizontal first path, advancing under tension second and third webs along a second path generally parallel to said first path and into a nip provided by a pair of rolls, applying adhesive to said second web prior to entry thereof into said nip, feeding a plurality of continuous elastic strands into said nip into contact with said adhesive, pressing said strands against aid adhesive equipped web just prior to said second web entering said nip, and shifting said strands laterally about leg opening areas in said second and third webs and partially wrapping said second and third webs about one of said rolls, and uniting thereafter said second and third webs with said first web, said steps including controlling the position of said strands closely adjacent said nip by passing said strands through eyelets of flat, resilient member means.

2. Apparatus for making disposable diaper comprising:
a frame defining a generally horizontal first path,
means on said frame for advancing a fluff pad-equipped first web along said first path,
a pair of rolls providing a nip mounted on said frame aligned with said first path and spaced therefrom,
a drum mounted on said frame in the space between said first path and said pair of rolls, one of said pair of rolls being positioned closely adjacent said drum,
means for advancing under tension along a second path second and third webs into the nip of said rolls, means in said second path for continuously equipping at least one of said webs with adhesive,
means for feeding a continuous elastic strand into said nip between said second and third webs and into contact with said continuous adhesive whereby said second and third webs are united and with said strand being united to said second and third webs,
said strand feeding means including guide means mounted on said frame closely adjacent said nip for shifting said strand laterally, and
roll means on said frame in said first path for cooperating with said drum for uniting said first web with the already united second and third webs,
said pair of rolls being positioned relative to said first path so as to have said united second and third webs travel in partial wrapping engagement with said one of said pair of rolls and in partial wrapping engagement with said drum until said first web is united with said already united second and third webs so as to maintain said elastic strand under tension while traveling between said nip and the union of said three webs taking place between said drum and said roll means.

3. The apparatus of claim 1 in which said adhesive equipping means is provided for each of said second and third webs.

4. Apparatus according to claim 1 in which said guide means includes a pair of spring members each having a plurality of eyelets therein for individually receiving a plurality of strands.

5. Apparatus for making disposable diaper comprising: a frame defining a generally horizontal first path, means on said frame for advancing a fluff pad-equipped first web along said horizontal path, a pair of rolls providing a nip mounted on said frame aligned with said first path and spaced therefrom, means for advancing under tension along a second path second and third webs into the nip of said rolls, means in said second path for equipping at least one of said webs with adhesive, means for feeding a continuous elastic strand into said nip between said second and third webs and into contact with said adhesive whereby said second and third webs are united and with said strand being united to said second and third webs, said strand feeding means including guide means mounted on said frame closely adjacent said nip for shifting said strand laterally, and means in said first path for uniting said first web with the already united second and third webs, said pair of rolls being positioned relative to said first path so as to have said united second and third webs travel in partial wrapping engagement with one of said pair of rolls, said guide means being generally flat and mounted to project into said nip to press said strand against said adhesive equipped web, said guide means being equipped with an eyelet through which said strand passes in wiping engagement with said guide means.

6. Apparatus for making disposable diapers comprising: a frame defining a generally horizontal path, means on said frame for advancing a fluff pad-equipped first web along said horizontal path, a pair of rolls providing a nip on said frame above and aligned with said path, means for advancing under tension along a second path second and third webs toward said pair of rolls, means on said frame for applying adhesive to at least one of said second and third webs prior to entry thereof into said nip, means for feeding a plurality of continuous elastic strands into said nip between said second and third webs, said strand feeding means including guide means transversely movably mounted on said frame for shifting said strands laterally, said guide means being mounted to press said strands against said adhesive equipped web, said guide means including a generally flat, resilient member positioned closely adjacent said nip, drum means for uniting said second and third webs with said first web, said pair of rolls being positioned adjacent said drum means for maintaining said second and third webs under tension until engagement with said first web, said apparatus including a pair of said generally flat, resilient members, one for each of said second and third webs, each said member having an eyelet and a portion adjacent said eyelet and positioned closely to one of said webs, said strand passing through said eyelet in wiping engagement with said portion to remove any adhesive thereon.

7. Apparatus for making disposable diaper comprising: a frame (14) defining a generally horizontal first path (P$_1$), means (24, 25) on said frame for advancing a fluff pad-equipped first web (27) along said first path, a pair of rolls (15, 16) providing a nip (17) mounted on said frame aligned with said first path and spaced therefrom, means for advancing along a second path (P$_2$) in said frame second and third webs (18, 19) into the nip (17) of said rolls, means (21) in said second path for equipping at least one of said webs with adhesive, means for feeding a continuous elastic strand (20) into said nip between said second and third webs are united and with said strand being united to said second and third webs characterized by, said strand feeding means (22, 23) including guide means mounted on said frame closely adjacent said nip for shifting said strand laterally, and means (24, 25) in said first path for uniting said first web with the already united second and third webs, said pair of rolls being positioned relative to said first path so as to have said united second and third webs (26) travel in partial wrapping engagement with one (16) of said pairs of rolls, said guide means being generally flat and mounted to project into said nip to press said strand against said adhesive equipped web, said guide means being equipped with an eyelet through which said strand passes in wiping engagement with said guide means.

8. Apparatus for making disposable diaper comprising: a frame (14) defining a generally horizontal first path (P$_1$), means (24, 25) on said frame for advancing a fluff pad-equipped first web (27) along said first path, a pair of rolls (15, 16) providing a nip (17) mounted on said frame aligned with said first path and spaced therefrom, means for advancing along a second path (P$_2$) in said frame second and third webs (18, 19) into the nip (17) of said rolls, means (21) in said second path for equipping at least one of said webs with adhesive, means for feeding a continuous elastic strand (20) into said nip between said second and third webs and into contact with said adhesive whereby said second and third webs are united and with said strand being united to said second and third webs characterized by, said strand feeding means (22, 23) including guide means mounted on said frame closely adjacent said nip for shifting said strand laterally, and means (24, 25) in said first path for uniting said first web with the already united second and third webs, said pair of rolls being positioned relative to said first path so as to have said united second and third webs (26) travel in partial wrapping engagement with one (16) of said pair of rolls, said guide means including a relatively elongated member having a first end portion, a transition portion and a second end portion, an eyelet in said second end portion, mounting means in said first end portion, said transition means being angled to dispose said first and second end portions in different planes.

9. The apparatus of claim 8 in which there are two guide means, each having a plurality of eyelets for directing a plurality of strands between said second and third webs.

10. Apparatus for making disposable diaper comprising: a frame (14) defining a generally horizontal first path (P$_2$), means (24, 25) on said frame for advancing a fluff pad-equipped first web (27) along said first path, a pair of rolls (15, 16) providing a nip (17) mounted on said frame aligned with said first path and spaced therefrom, means for advancing along a second path (P$_2$) in said frame second and third webs (18, 19) into the nip (17) of said rolls, means (21) in said second path for equipping at least one of said webs with adhesive, means for feeding a continuous elastic strand (20) into said nip between said second and third webs and into contact with said adhesive whereby said second and third webs are united and with said strand being united to said second and third webs characterized by, said strand feeding means (22, 23) including guide means mounted on said frame closely adjacent said nip for shifting said strand laterally, and means (24, 25) in said first path for uniting said first web with the already united second and third webs, said pair of rolls being positioned relative to said first path so as to have said united second and third webs (26) travel in partial wrapping engagement with one (16) of said pair of rolls, said strand feeding means including a subframe mounted on said frame (14), cylinder means (53) interconnecting said frame and subframe to pivot said subframe and withdraw said guide means (23) from said nip (17).

11. The apparatus of claim 10 in which said frame is equipped with a cross shaft (60) pivotally mounted in the side frames (14a, 14b) of said frame, an L-shaped arm (59) fixed to said cross shaft and carrying one of said rolls (15) at one end thereof, second cylinder means (56) interconnected between said frame and the other end of said L-shaped arm; and means (61, 62, 63) associated with said cross shaft (60) and other roll (16) for pivoting said other roll away from said uniting mean (26).

* * * * *